United States Patent
Sood et al.

[11] Patent Number: 6,090,062
[45] Date of Patent: Jul. 18, 2000

[54] PROGRAMMABLE ANTISIPHON SHUNT SYSTEM

[75] Inventors: Sandeep Sood, Dearborn; Alexa I. Canady, West Bloomfield; Steven D. Ham, Mt. Clemens, all of Mich.

[73] Assignee: Wayne State University, Detroit, Mich.

[21] Appl. No.: 09/086,891

[22] Filed: May 29, 1998

[51] Int. Cl.$^7$ .............................. A61M 5/00; A61M 1/00; A61M 11/00

[52] U.S. Cl. .................................. 604/9; 604/28; 604/30; 604/93; 604/133

[58] Field of Search ..................................... 604/8–10, 30, 604/27–28, 43, 131, 133, 523, 533, 537, 540, 93

[56] References Cited

U.S. PATENT DOCUMENTS

| | | | |
|---|---|---|---|
| 3,601,128 | 8/1971 | Hakim | 604/9 |
| 3,654,932 | 4/1972 | Newkirk et al. . | |
| 4,103,689 | 8/1978 | Leighton . | |
| 4,281,666 | 8/1981 | Cosman | 128/748 |
| 4,364,395 | 12/1982 | Redmond et al. . | |
| 4,537,387 | 8/1985 | Danby et al. . | |
| 4,551,128 | 11/1985 | Hakim et al. . | |
| 4,557,721 | 12/1985 | Hooven . | |
| 4,595,390 | 6/1986 | Hakim et al. | 604/9 |
| 4,598,579 | 7/1986 | Cummings et al. | 604/9 |
| 4,741,730 | 5/1988 | Dormandy, Jr. . | |
| 4,776,838 | 10/1988 | Sainte-Rose et al. | 604/9 |
| 4,776,839 | 10/1988 | Doumenis | 604/9 |
| 4,867,741 | 9/1989 | Portnoy . | |
| 4,950,232 | 8/1990 | Ruzicka et al. . | |
| 5,167,615 | 12/1992 | East et al. . | |
| 5,191,898 | 3/1993 | Millar | 604/8 |
| 5,192,265 | 3/1993 | Drake et al. . | |
| 5,226,886 | 7/1993 | Skakoon et al. . | |
| 5,281,210 | 1/1994 | Burke et al. . | |
| 5,437,627 | 8/1995 | Lecuyer . | |
| 5,637,083 | 6/1997 | Bertrand et al. | 604/9 |
| 5,643,195 | 7/1997 | Drevet . | |
| 5,662,600 | 9/1997 | Watson et al. . | |
| 5,687,614 | 11/1997 | Hashimoto et al. | 74/459 |
| 5,928,182 | 7/1999 | Kraus et al. | 604/9 |

FOREIGN PATENT DOCUMENTS

| | | |
|---|---|---|
| 2 698 535 A1 | 11/1992 | France . |
| 41 40 251 A1 | 12/1991 | Germany . |

OTHER PUBLICATIONS

A. Aschoff, et al. "Overdrainage and Shunt Technology", Child Nerv. Syst (1995) 11:193–202.

M. Czosnyka, et al., "Hydrodynamic Properties of Hydrocephalus Shunts: United Kingdom Shunt Evaluation Laboratory".

C. Kadowaki, et al., "CSF Shunt Physics: Factors influencing Inshutn CSF Flow" Child Nerv System (1995) 11:203–206.

R.W.P. Cutler, et al., "Formation and Absorption of Cerebrospinal Fluid in Man" pp. 707–720.

William O. Bell, "Cerebrospinal Fluid Reabsorption" Concepts in Pediatric Neurosurgery, 1990, vol. 10, pp. 214–234.

(List continued on next page.)

*Primary Examiner*—Mark O. Polutta
*Assistant Examiner*—Patricia Bianco
*Attorney, Agent, or Firm*—Brooks & Kushman P.C.

[57] ABSTRACT

A surgically implantable shunt system 20 is provided for controlling fluid flow from a relatively high pressure region to a low pressure region. The system 20 includes a rigid housing 22 defining a sealed chamber 24 therewithin, the housing 22 having an inlet port 26 in fluid communication with the high pressure region, and an outlet port 28 in fluid communication with the low pressure region. A conduit 44 extends through the housing 22 from the inlet port 26 to the outlet port 28 and includes a valve 46 disposed within the sealed chamber 24. The valve 46 regulates fluid flow from the high pressure region to the low pressure region, wherein operation of the valve 46 is dependent upon a pressure $P_c$ external to the conduit 44 and within the sealed chamber 24, and is not susceptible to changes in pressure outside the housing 22.

20 Claims, 2 Drawing Sheets

OTHER PUBLICATIONS

Albert N. Martins et al., "Dynamics of the cerebrospinal fluid and the spinal dura matter", Journal of Neurology, Neurosurgery and Psychiatry, 1972, 35, 468–473.

Takashi Iwabuchi, et al., "Dural Sinus Pressure as Related to Neurosurgical Positions", Neurosurgery vol. 12, No. 2, 1983, pp. 203–207.

James M. Drake, et al. "Functional Obstruction of an Anti–siphon Device by Raised Tissue Capsule Pressure", Neurosurgery, vol. 32, No. 1, Jan. 1993, pp. 137–139.

Marcia C. da Silva, et al., "Effect of Subcutaneous Implantation of Anti–Siphon Devices on CSF Shunt Function", Pediatr Neurosurg 1990–91:16:197–202.

Carol K. Lyon, et al., "Flow through Collapsible Tubes at Low Reynolds Numbers" Circulation Research, vol. 47, No. 1, Jul. 1980, pp. 68–73.

Ascher H. Shapiro, "Steady Flow in Collapsible Tubes", Journal of Biomechanical Engineering, Aug. 1977 99:126–147.

Dali J. Patel, et al., "Basic Hemodynamics and Its role in Disease Processes" pp. 408–424.

Harold D. Portnoy, et al., Anti–siphon and reversible occlusion valves for shunting in hydrocephalus and preventing post–shunt.

S. Pauly "Permeability and Diffusion Data", Polymer Handbook, 1989, vol. 1, pp. 435—449.

Roger D. Kamm, "Flow through Collpasible Tubes" Handbook of Bioengineering, 1987, pp. 23.1—23.17.

PROGRAMMABLE ANTISIPHON SHUNT SYSTEM

TECHNICAL FIELD

This invention relates to devices used in the management of patients with hydrocephalus, and in particular to antisiphon devices used to counteract postural intracranial hypotension related to overdrainage of cerebrospinal fluid.

BACKGROUND ART

Hydrocephalus is a disease in which the body is unable to remove cerebrospinal fluid (CSF) from the ventricles of the brain, usually due to the blockage of natural drainage paths. As a result, CSF accumulates within the skull and causes increased intracranial pressure. This increased pressure, in turn, causes adverse physiological effects including compression of brain tissue, impairment of blood flow, and impairment of normal brain metabolism.

Hydrocephalus is usually treated by installing a shunt system for draining excess CSF in a controlled manner from the production site, the cerebral ventricles, to a resorption site elsewhere in the body, such as the peritoneal cavity or the right atrium. The shunt system typically includes a proximal catheter inserted into the ventricle which is connected distally to a catheter that conducts fluid to the resorption site. To control the flow of CSF and maintain the proper pressure in the ventricles, a valve is placed in the conduit between the brain and the resorption site.

Many shunt systems simply utilize the differential fluid pressure between the production site and the resorption site to control fluid flow. However, when a patient rises from a supine position to a seated or standing position, the differential fluid pressure between the production and resorption sites normally increases due to the elevation of the brain compared with the selected drainage location elsewhere in the body. This increase in the pressure differential due to hydrostatic factors can result in overdrainage, or siphoning, of CSF from the cerebral ventricles. Failure to recreate physiological CSF outflow may result in significant stress in the cerebral tissues which in the long term can lead to effects like slit ventricle syndrome, changes in the brain compliance from glial cell hypertrophy, chronic headaches, and subdural hematomas.

More recently, antisiphon shunt systems have been developed which minimize overdrainage in upright posture to maintain pressures within limits which would normally be provided by physiological mechanisms regardless of orientation. In contrast to standard differential pressure valves, antisiphon valves close whenever the cerebral ventricular pressure becomes subatmospheric, thus eliminating siphoning effects when a patient stands. Whenever the ventricular pressure rises above atmospheric pressure, the valve opens, thus regulating ventricular pressure within a more normal range. Consequently, flow is controlled predominantly by the differential between the proximal, ventricular pressure and atmospheric pressure, rather than by the differential pressure between the production and resorption sites.

As described above, proper functioning of an antisiphon device requires exposure of the valve to atmospheric pressure. As a result, the valves are typically enclosed in chambers having walls which are deformable or are provided with apertures therein, thereby rendering the valves susceptible to changes in external, subcutaneous pressure. By construction, an increase in subcutaneous pressure above atmospheric pressure will increase the pressure within the chamber and, consequently, increase the resistance to flow. Subcutaneous fibrotic scarring which inevitably develops around the site of shunt implantation can cause significant increases in external pressure, resulting in underdrainage of CSF through the antisiphon shunt system.

SUMMARY OF THE INVENTION

Therefore, it is a principal object of the present invention to provide a surgically implantable shunt system which is effective in draining CSF in response to abnormal intracranial pressures, avoids overdrainage in the event of normal variations in fluid pressure, and avoids underdrainage due to increases in subcutaneous pressure.

It is another object of the present invention to provide an antisiphon shunt system in which the drainage pressure is adjustable in order to suit the individual pressure requirements of each patient.

Accordingly, a surgically implantable shunt system is provided for controlling fluid flow from a relatively high pressure region to a low pressure region. The system includes a rigid housing defining a sealed chamber therewithin, the housing having an inlet port in fluid communication with the high pressure region, and an outlet port in fluid communication with the low pressure region. A conduit extends through the housing from the inlet port to the outlet port and includes a valve disposed within the sealed chamber. The valve regulates fluid flow from the high pressure region to the low pressure region, wherein operation of the valve is dependent upon a pressure $P_c$ external to the conduit and within the sealed chamber, and is not susceptible to changes in pressure outside the housing.

In a preferred embodiment, a flexible diaphragm is positioned within the sealed chamber. The diaphragm subdivides the sealed chamber, and creates a volume $V_c$ in which the valve is disposed. The diaphragm may be positioned to vary $V_c$, and therefore the pressure $P_c$ therein. A regulator, preferably a magnetic screw, in communication with the diaphragm is used to position the diaphragm. Variation of the pressure $P_c$ will affect the operation of the valve, such that the drainage pressure of the shunt system can be adjusted to meet the needs of individual patients.

The above objects and other objects, features, and advantages of the present invention are more readily understood from a review of the attached drawings and the accompanying specification and claims.

BEST MODES FOR CARRYING OUT THE INVENTION

Figure 1:
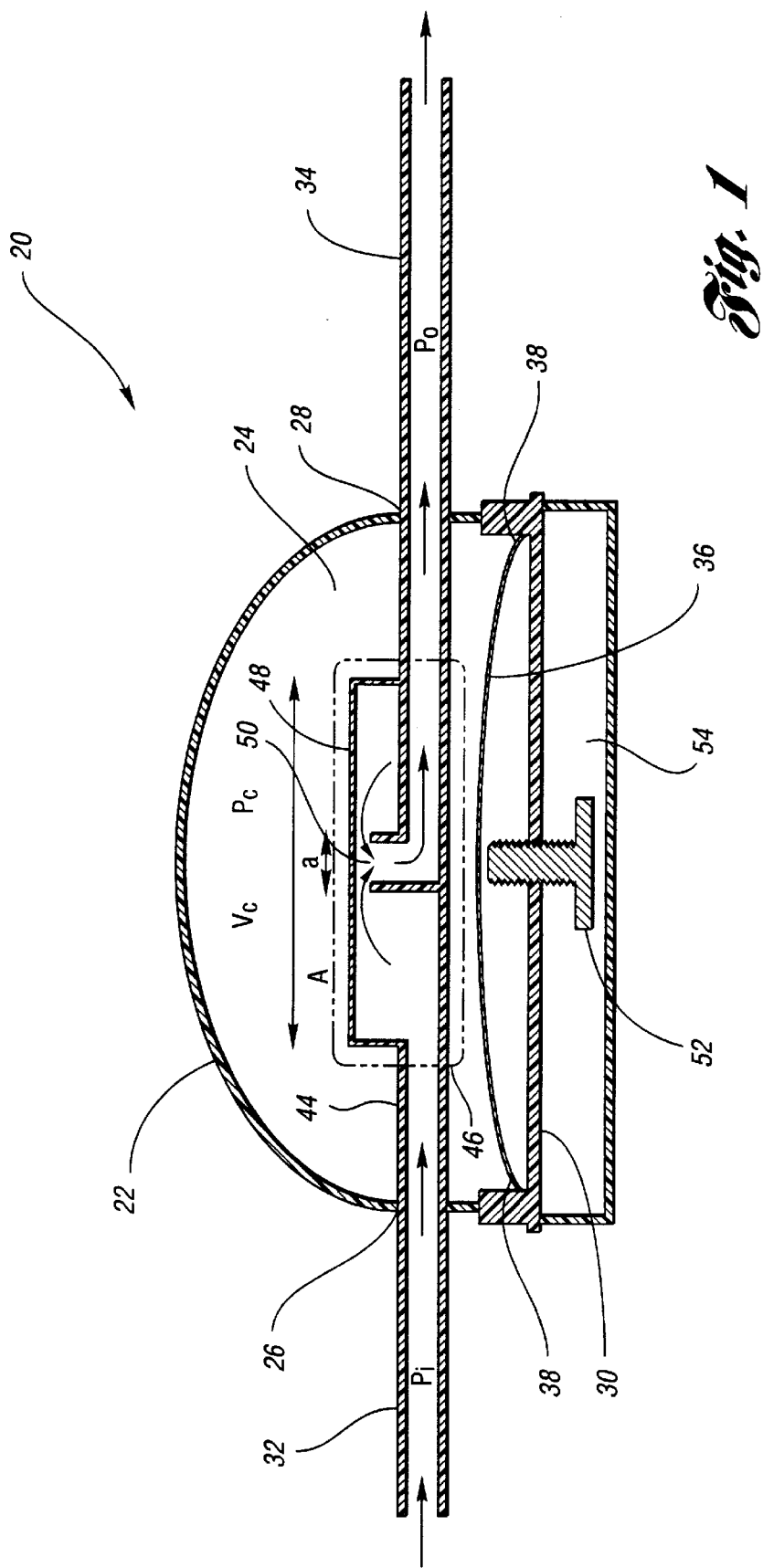
FIG. 1 is a sectional view of a programmable antisiphon shunt system constructed in accordance with the present invention.

Referring first to FIG. 1, a surgically implantable shunt system 20 constructed in accordance with the present invention is shown. Shunt system 20 includes a rigid housing 22 defining a sealed chamber 24 therewithin. Housing 22 is preferably constructed from a high molecular weight polymer such as polyacrylonitrile (PAN), polyvinylidene chloride (SARAN®), or polycarbonates (LEXAN®) which have very low permeability to gases such as oxygen, nitrogen, and sulfur hexafluoride, respectively. Further details regarding the permeability of the various polymers listed above may be found in Pauly S, Permeability and Diffusion Data, In: Polymer Handbook, $3^{rd}$ edition, Brandrup J, Immergut EH, eds., John Wiley & Sons, New York, 1989, pp. 435–449, which is herein incorporated by reference.

The permeability of housing 22 may be further reduced by vacuum metallization or metal foil lamination. Housing 22 is lined externally by a medical grade silicone elastomer, and in a preferred embodiment is constructed to be 2.5 cm in length, 1.5 cm in diameter, and 0.8 to 1 cm in height. In sharp contrast to prior art shunt systems, housing 22 is not deformable, nor in fluid communication with atmospheric pressure. Therefore, sealed chamber 24 has a pressure $P_c$ which is not susceptible to changes in external, subcutaneous pressure.

Housing 22 includes an inlet port 26 in fluid communication with a high pressure region having a pressure $P_i$, typically the cerebral ventricles, containing CSF under pressure to be relieved. An outlet port 28 is provided at the opposite end of housing 22 and is in fluid communication with a low pressure region having a pressure $P_o$, typically the peritoneal cavity, the right atrium, or another suitable drainage location. Housing 22 also contains a substantially flat base 30. In a preferred embodiment, base 30 is shaped so as to approximate the contour of the human skull adjacent which shunt system 20 is implanted.

Shunt system 20 preferably includes a proximal catheter 32 sealingly connected to inlet port 26 and in fluid communication with the high pressure region, as well as a distal catheter 34 sealingly connected to outlet port 28 and in fluid communication with the low pressure region. Typically, catheters 32 and 34 comprise silastic tubing, preferably having an inside diameter of 1.3 mm.

A conduit 44 extends through housing 22 from inlet port 26 to outlet port 28. Conduit 44 includes a valve 46 which comprises a pressure-sensitive membrane 48 and a flow orifice 50. Membrane 48 should be composed of a material with very low gas permeability, such as those recited above for housing 22. Membrane 48 is positioned to selectively occlude flow orifice 50 in response to a sufficient pressure differential across membrane 48 in order to close valve 46 and prohibit fluid flow therethrough. Flow orifice 50 may be centrally located as shown in FIG. 1 or, alternatively, may be offset toward outlet port 28 to provide enhanced flow control. In shunt system 20 of the present invention, valve 46 has no free moving components, and is therefore relatively unsusceptible to vibrations from body movements.

For a given pressure gradient ($P_i$–$P_o$), fluid flow through valve 46 occurs when the total force acting downward on membrane 48 is exceeded by the force acting upward on membrane 48. When valve 46 is closed, downward forces are provided by pressure $P_c$ over the entire area A of membrane 48, in addition to the pull from the negative pressure $P_o$ over a small fraction of membrane 48, designated as a. An upward force on membrane 48 is provided by the inlet pressure $P_i$ multiplied by the area (A–a). Therefore, valve 46 opens when:

$$P_i*(A-a) > P_c*A + P_o*a \qquad (1)$$

Rearranging equation (1), and substituting f for a/A, the equation becomes:

$$P_i > (P_c + f*P_o)/(1-f) \qquad (2)$$

Thus, for typical ratios of a to A, the opening pressure of valve 46 is predominately dependent upon $P_i$ and $P_c$, with only a small fraction of $P_o$ contributing to the function of valve 46.

In a preferred embodiment, a flexible diaphragm 36, preferably constructed of a material with very low gas permeability such as those recited above for housing 22, is positioned within sealed chamber 24 of housing 22. Diaphragm 36 has edges 38 which are attached to base 30 through adhesives, welding, or the like. With this configuration, diaphragm 36 subdivides sealed chamber 24, and creates a volume $V_c$ in which valve 46 is disposed. The pressure $P_c$ inside sealed chamber 24 may then be adjusted by the movement of diaphragm 36 to either increase or decrease volume $V_c$, thereby affecting the operation of valve 46.

In order to selectively position diaphragm 36 within chamber 24, a regulator, preferably a magnetically polarized screw 52, is utilized in communication with diaphragm 36. Alternatively, a preset screw could be used to adjust diaphragm 36 mechanically at the time of surgery. In yet another embodiment, either magnetic screw 52 or a preset screw is provided with a plunger occupying the entire cross-sectional area of sealed chamber 24 to alter volume $V_c$ therein, thereby eliminating the need for diaphragm 36.

In the preferred embodiment, magnetic screw 52 is threaded into base 30, and is contained within an auxiliary housing 54. Magnetic screw 52 includes a permanent magnet (not shown) having well-defined north and south poles. Magnetic screw 52 can be adjusted to any position using an external magnetic field, as is well known in the art. Typically, the intensity of the external magnetic field required to turn screw 52 is high enough that other magnetic fields a patient may encounter will have no effect on the position of screw 52. Alternatively, a locking mechanism could be used to secure the position of screw 52.

Magnetic screw 52 can be used to adjust the drainage pressure for individual patients. After implantation of shunt system 20, the intracranial pressure of a patient, usually in an upright position, is typically monitored for 24 to 48 hours, allowing a physician time to adjust the pressure $P_c$ within sealed chamber 24 to the optimum level for that specific individual. Magnetic screw may also be utilized as a calibration mechanism. Due to the very low permeability of diaphragm 36, pressure-sensitive membrane 48, and housing 22, a pressure drift within sealed chamber 24 can be kept under 1 mm $H_2O$ per year by the appropriate choice of material and gas. Magnetic screw 52 can be used to adjust pressure $P_c$ back to the optimum level originally set by the physician.

Figure 2:
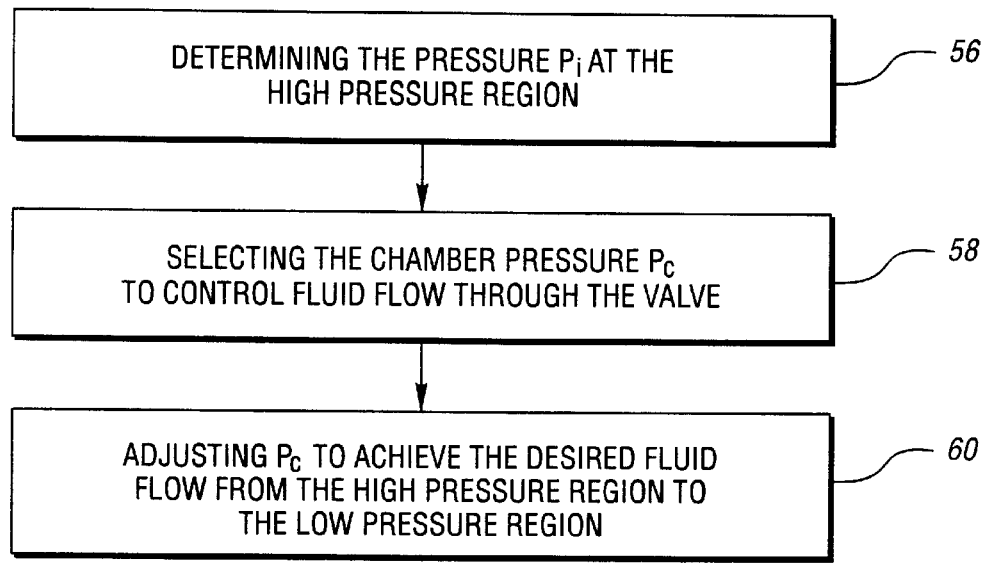
FIG. 2 outlines a preferred method of using the shunt system of the present invention.

A preferred method of using shunt system 20 to control fluid flow in a patient is outlined in FIG. 2. In practice, as shown in block 56, a physician will determine the pressure $P_i$ at the high pressure region, typically the intracranial pressure, by monitoring the patient for a period of time after implantation of shunt system 20. As explained above, the value of $P_o$ has a relatively insignificant effect on the function of valve 46. Next, the physician can select the appropriate value of $P_c$ as shown in block 58 to control $P_i$ and fluid flow optimally for that particular patient. Lastly, in block 60, the physician will then adjust $P_c$, preferably non-invasively via magnetic screw 52, to achieve the desired fluid flow from the high pressure region to the low pressure region.

Figure 3:
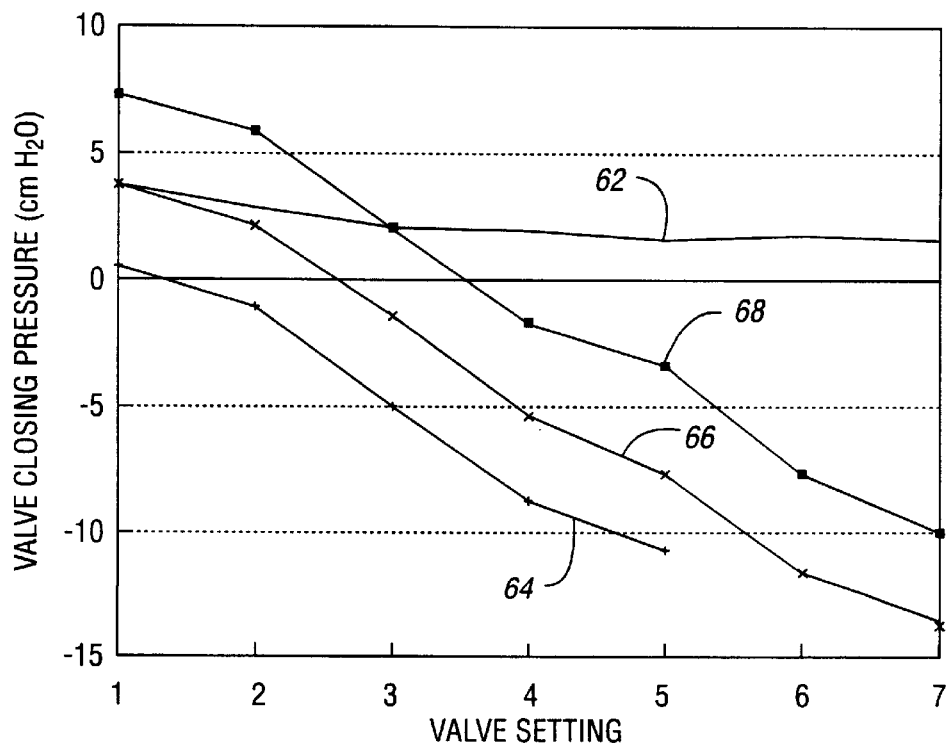
FIG. 3 is a graph depicting the operational capabilities of the shunt system of the present invention at different outlet pressures and for different valve settings.

Experiments were conducted to evaluate the pressure-flow characteristics and the ability to adjust drainage pressures of shunt system 20 of the present invention. Valve 46 was connected to a distal catheter 34 which was 90 cm in length, and the closing pressure of valve 46 was measured with a manometer at different valve settings. In these experiments, a regular screw, instead of magnetic screw 52, was used such that seven discrete positions of diaphragm 36 were set mechanically. Referring to FIG. 3, measurements of valve closing pressure were taken where $P_o$ was set equal to 0, −15, −30, and −45 cm $H_2O$, as indicated by lines 62, 64, 66, and 68, respectively. As shown, the closing pressure of valve 46 decreases linearly with the valve setting for each value of $P_o$, providing a wide range of drainage pressures to suit the needs of individual patients.

While CSF drainage from the cerebral ventricles is disclosed herein as the best known use for this device, it is evident that the device is also useful to drain other fluids from other body regions.

It is understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. A surgically implantable shunt system for controlling fluid flow from a relatively high pressure region having a pressure $P_i$ to a low pressure region having a pressure $P_o$, the system comprising:

a rigid housing defining a sealed chamber therewithin, the housing having an inlet port in fluid communication with the high pressure region and an outlet port in fluid communication with the low pressure region;

a valve disposed within the sealed chamber for regulating fluid flow from the high pressure region to the low pressure region;

a flexible diaphragm that subdivides the sealed chamber and creates a volume $V_c$ in which the valve is disposed; and a regulator for adjusting a pressure $P_c$ within the sealed chamber by selectively positioning the diaphragm;

wherein operation of the valve is substantially dependent on $P_i$ and $P_c$, and is not susceptible to changes in pressure outside the housing or a differential pressure between $P_i$ and $P_o$.

2. The shunt system of claim 1, wherein the valve comprises a pressure-sensitive membrane and a flow orifice, wherein the membrane is positioned to selectively occlude the flow orifice in order to close the valve and prohibit fluid flow therethrough.

3. The shunt system of claim 2, wherein the location of the flow orifice within the valve is offset toward the outlet port.

4. The shunt system of claim 2, wherein the pressure-sensitive membrane is constructed from a high molecular weight polymer with very low gas permeability.

5. The shunt system of claim 1, wherein the pressure $P_c$ is different from atmospheric pressure.

6. The shunt system of claim 1, further comprising a locking mechanism for securing the regulator in position.

7. The shunt system of claim 1, wherein the regulator comprises a magnetic screw which can be adjusted non-invasively.

8. The shunt system of claim 1, wherein the regulator comprises a preset screw which can be adjusted mechanically at the time of surgery.

9. The shunt system of claim 1, wherein the diaphragm is constructed from a high molecular weight polymer with very low gas permeability.

10. The shunt system of claim 1, further comprising a catheter sealingly connected to the inlet port and in fluid communication with the high pressure region.

11. The shunt system of claim 1, further comprising a catheter sealingly connected to the outlet port and in fluid communication with the low pressure region.

12. The shunt system of claim 1, wherein the housing further comprises a base which is substantially flat and shaped to approximate the contours of a human skull.

13. The shunt system of claim 1, wherein the housing is constructed from a high molecular weight polymer with very low gas permeability.

14. The shunt system of claim 1, wherein the housing is treated by vacuum metallization or metal foil lamination.

15. The shunt system of claim 1, wherein the housing is lined externally by a medical grade silicone elastomer.

16. A method of using a surgically implantable shunt system for controlling fluid flow from a relatively high pressure region having a pressure $P_i$ to a low pressure region having a pressure $P_o$, wherein the shunt system comprises a rigid housing defining a sealed chamber therein, the housing having an inlet port in fluid communication with the high pressure region, an outlet port in fluid communication with the low pressure region, and a valve disposed within the sealed chamber, the method comprising:

determining the pressure $P_i$ at the high pressure region;

selecting a pressure $P_c$ within the sealed chamber to control the operation of the valve in order to regulate fluid flow from the high pressure region to the low pressure region, wherein operation of the valve is substantially dependent on $P_i$ and $P_c$, and is not susceptible to changes in pressure outside the housing or a differential pressure between $P_i$ and $P_o$; and adjusting the pressure $P_c$ by subdividing the sealed chamber and varying a volume $V_c$ in which the valve is disposed, thereby achieving the desired fluid flow from the high pressure region to the low pressure region.

17. The method of claim 16, wherein adjusting the pressure $P_c$ includes moving a regulator to selectively position a flexible diaphragm within the sealed chamber.

18. The method of claim 17, further comprising securing the regulator in position.

19. The method of claim 16, wherein determining the pressure $P_i$ comprises monitoring the intracranial pressure of a patient in whom the shunt system is implanted.

20. The method of claim 16, wherein adjusting the pressure $P_c$ is accomplished non-invasively.

* * * * *